United States Patent [19]

Russell

[11] Patent Number: 4,779,291

[45] Date of Patent: Oct. 25, 1988

[54] MEDICAL EYE SHIELD

[76] Inventor: John P. Russell, 1000 Main St., Gardendale, Ala. 35071

[21] Appl. No.: 78,553

[22] Filed: Jul. 28, 1987

[51] Int. Cl.⁴ .......................... A61F 9/02; G02C 9/00
[52] U.S. Cl. .......................................... 2/439; 2/435; 2/440; 2/450; 351/41; 351/43
[58] Field of Search .................. 2/431, 426, 439, 440, 2/206, 450, 435; 357/156, 157, 158, 111, 43, 41; 128/132 R, 163

[56] References Cited

U.S. PATENT DOCUMENTS

| | | | |
|---|---|---|---|
| 599,289 | 2/1898 | Stevens | 2/439 |
| 1,123,376 | 1/1915 | Rextrew | 2/431 X |
| 1,190,674 | 7/1916 | Rextrew | 2/440 |
| 1,800,051 | 4/1931 | Blanco | 2/206 |
| 2,280,098 | 4/1942 | Moss | 2/435 |
| 2,389,707 | 11/1945 | Wylde et al. | 2/431 |
| 3,502,396 | 3/1970 | Greenberg | 351/157 |
| 4,122,847 | 10/1978 | Craig | 128/132 R |
| 4,494,251 | 1/1985 | Ainsworth et al. | 2/426 X |
| 4,520,510 | 6/1985 | Daigle | 2/426 X |

FOREIGN PATENT DOCUMENTS

| | | | |
|---|---|---|---|
| 1016444 | 11/1952 | France | 2/439 |
| 489530 | 7/1938 | United Kingdom | 2/431 |

OTHER PUBLICATIONS

"Safe T Guard", directions by Madison Dental Co. pub. 12/70.

Primary Examiner—Stuart S. Levy
Assistant Examiner—Joseph J. Hail, III
Attorney, Agent, or Firm—George A. Bode

[57] ABSTRACT

A shield comprising a thin elongated transparent flexible member having an upper flat edge, a pair of spaced convex edges spaced apart and located opposite the flat edge for forming a pair of spaced planar portions. The planar portions extend between the flat edge and the convex edges, with the convex edges being joined by a concave edge located opposite the flat edge and between the convex edges which defines a narrowed webbed portion extending integrally between the planar portions. An elongated deformable flexible sealing member extends along the flat edge between the distal ends of the flexible member and a second elongated deformable flexible sealing member extends continuously along the convex edges and the concave edge between the distal ends of the flexible member. An elongated band connected between the distal ends of the flexible member attaches the flexible member in an arcuate shape around the head with the spaced planar surfaces located above and covering the eyes and the web portion extending transversely across the nose. The sealing members contact and seal against the body portion around the eyes along the length of the seal members.

19 Claims, 3 Drawing Sheets

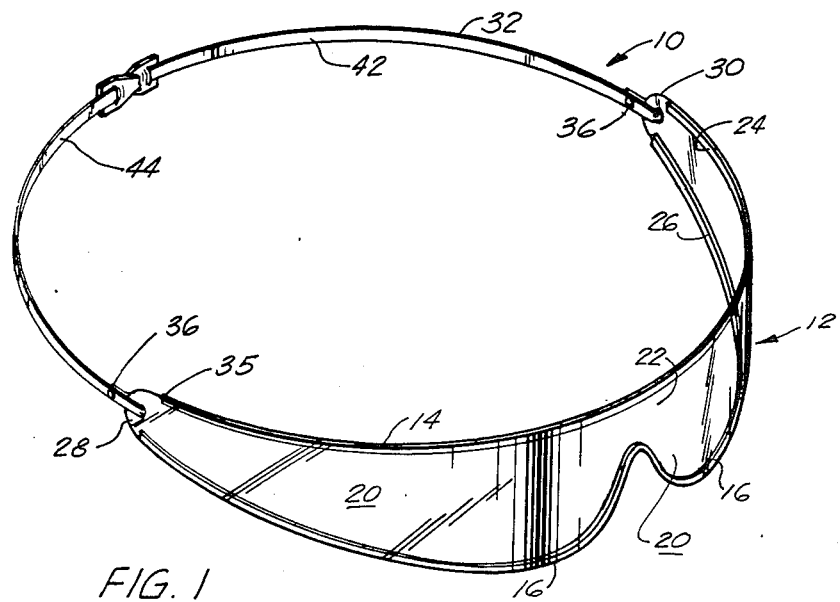
FIG. 1
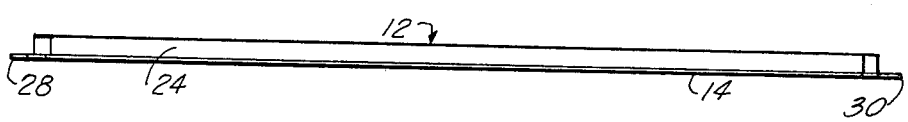
FIG. 4
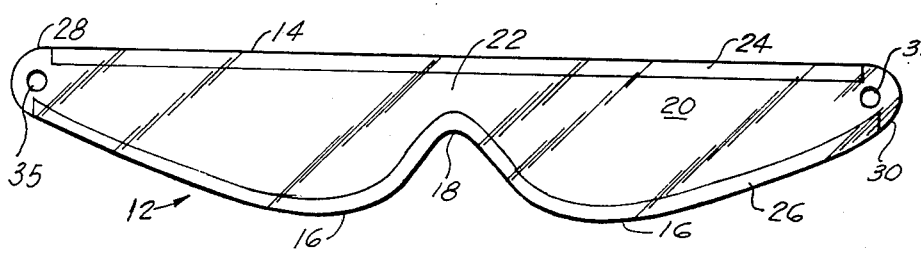
FIG. 2  FIG. 3
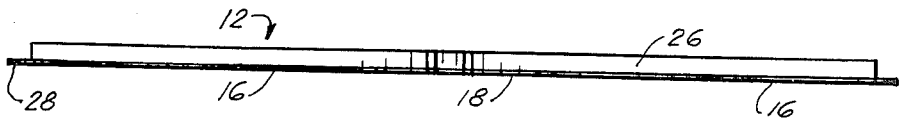
FIG. 5
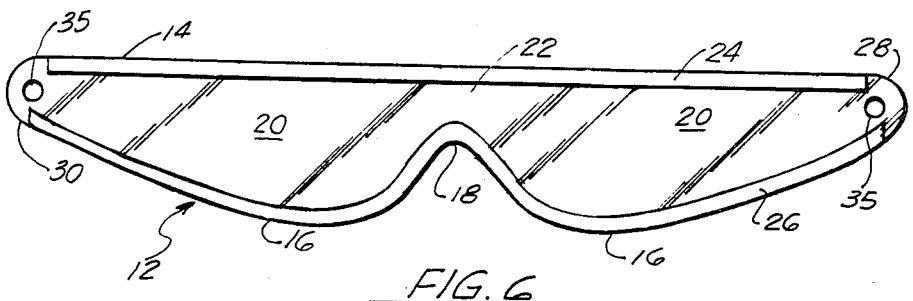
FIG. 6

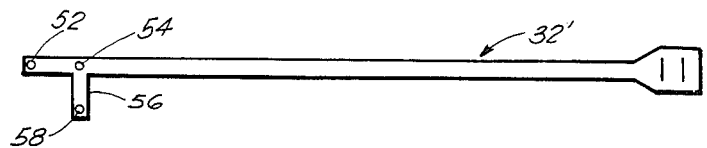
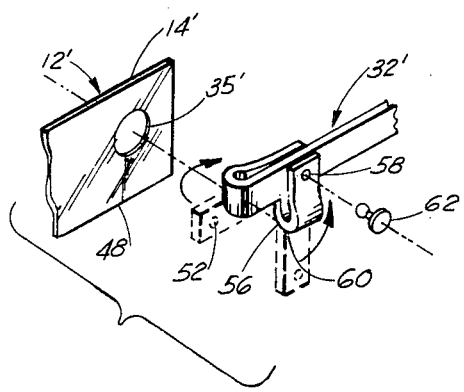
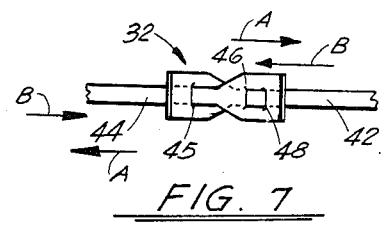
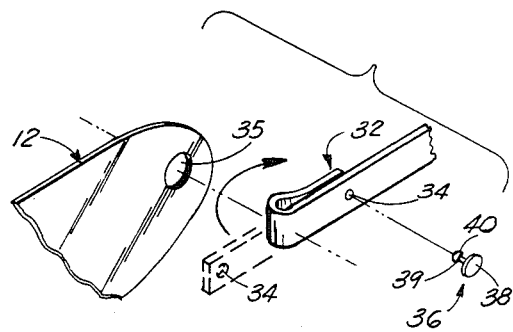
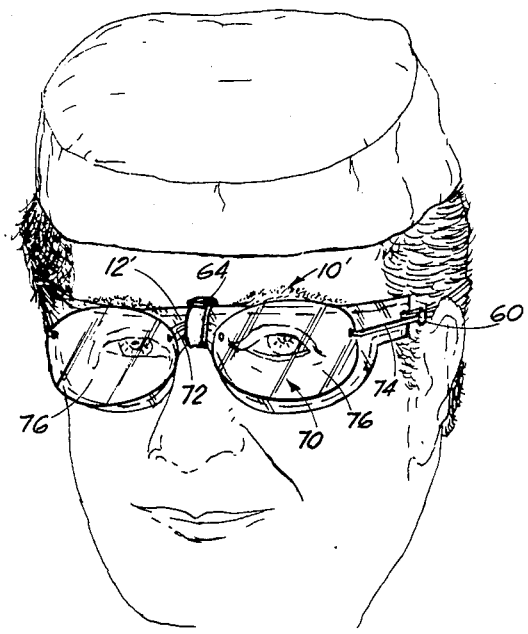
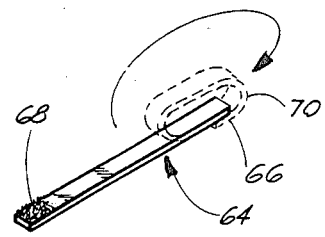

MEDICAL EYE SHIELD

BACKGROUND OF THE INVENTION

1. Field of the Invention

The present invention relates to goggles and more particularly to disposable goggles having a transparent flexible member which includes integral planar surfaces separated by a narrowed web portion formed integral with the planar surfaces that when the flexible elongated member is curved or positioned over the eyes, elongated deformable flexible sealing members which extend along the periphery of the flexible member are sealed against the body portions around the eyes for preventing foreign matter from being splattered into the eyes.

2. General Background

With communicable diseases such as AIDS, it is possible to transmit the disease to innocent victims such as physicians and their assistants by the accidental splattering of blood during surgical procedures, for example, into the eyes of the surgeon or assistant. Since the blood may be contaminated, any covering which would be provided for the eyes should be disposable to avoid the likelihood of spreading the disease from contaminated material which remains on eye coverings in the event the article is reused.

However, no suitable shield at present exist which is suitable for use in surgical procedures to cover the eyes and which is disposable after use.

Hence, an object of the present invention is to provide a shield which covers the eyes and which includes sealing members which contact the body portion around the eyes for preventing blood from splattering into the eyes. In accordance with this object, it is further an object of the present invention that the shield be disposable.

Another object of the present invention is that the shield be inexpensive and easy to make so that its cost will be low.

Other objects and advantages of the present invention will become apparent from a consideration of the following detailed description and drawings.

SUMMARY OF THE PRESENT INVENTION

In accordance with the above objects, the shield according to the present invention includes an elongated transparent flexible member having integral symmetrical spaced planar surfaces joined by an integral narrowing webbed portion. The elongated sealing members are sealably attached to the interior surface of the flexible member along its upper edge and its lower edge. An adjustable band is included between the ends of the flexible member and holds the flexible member in position with the planar portions curved and covering the eyes of the user. Adjustment of the adjustable band by the user allows the sealing members to be pressed against the body portions around the eyes thus, preventing foreign matter which has been splattered, for example, from entering the eyes between the sealing members and the body portions thereof in contact.

The second preferred embodiment of the shield according to the present invention includes tabs which extend laterally from the attachment band which are folded over to form lateral retainers through which the bridge piece of the user's glasses is inserted for retaining the glasses in a position having the ear pieces alongside and parallel to the band of the shield when the ear pieces are hooked over the ears. A flexible bridge retainer having velcro portions thereon on opposing faces of its ends is wrapped around the web portion of the flexible member and the opposing velcro portions are then mated together with the bridge piece of the glasses between the flexible member and the web portion of the flexible member. The velcro portions are pressed together and mated thus, allowing the bridge piece of the glasses to be retained over the web portion of the elongated flexible member. Thus, the bridge piece of the glasses is lifted off of the nose and the glasses are held in a position off of the nose, with their spectacle portions lying over the planar portions.

After use, the shield is removed from the head of the user and suitably discarded along with other infected disposables.

BRIEF DESCRIPTION OF THE DRAWING

For a further understanding of the nature and objects of the present invention, reference should be had to the following description taken in conjunction with the accompanying drawing in which like parts are given like reference numerals and, wherein:

FIG. 1 is a perspective view of the first preferred embodiment of the medical shield according to the present invention showing its elongated transparent flexible member and elongated band;

FIG. 2 is a front planar view of the transparent flexible member of the preferred embodiment of FIG. 1;

FIG. 3 is a side planar view of the transparent flexible member of the preferred embodiment of FIG. 1;

FIG. 4 is a top planar view of the transparent flexible member of the preferred embodiment of FIG. 1;

FIG. 5 is a bottom planar view of the transparent flexible member of the preferred embodiment of FIG. 1;

FIG. 6 is a rear planar view of the transparent flexible member of the preferred embodiment of FIG. 1;

FIG. 7 is a detail of the elongated band of the preferred embodiment of FIG. 1;

FIG. 8 is a perspective partial detail showing the attachment of the elongated band to the flexible member of the preferred embodiment of FIG. 1;

FIG. 15 is a side view of one of the flexible elongated members of the elongated band of FIG. 9;

FIG. 16 is a perspective detail showing attatchment of the elongated band of FIG. 9 to the transparent flexible member of FIG. 9;

FIG. 17 is a perspective detail of the elongated flexible bridge retainer of FIG. 9 which is wrapped as indicated by the dashed lines of the figure around the web portion of the elongated transparent flexible member; and, FIG. 18 is an application of the second embodiment of FIG. 9 shown attached around the head of a user.

DETAILED DESCRIPTION OF THE PREFERRED EMBODIMENT

Figure 9:
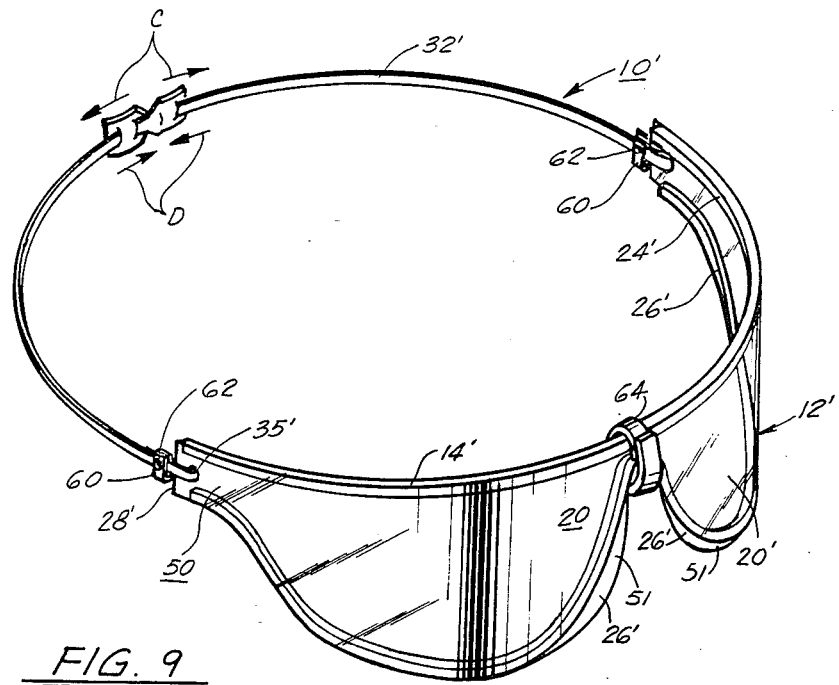
FIG. 9 is a perspective view of the second preferred embodiment of the medical shield according to the present invention showing its elongated transparent flexible member, elongated band and elongated flexible bridge retainer.
Figure 12:
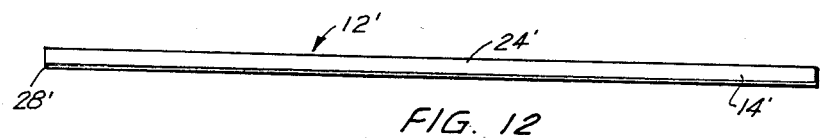
FIG. 12 is a top planar view of the transparent flexible member of the second embodiment of FIG. 9.

Referring now more specifically to the drawings, reference numeral 10 in FIGS. 1-6 is used to generally designate the first preferred embodiment of the medical shield 10 according to the present invention. Shield 10 includes an elongated transparent flexible member 12. Flexible member 12 is a crystal clear, colorless polyester film, VISTEX-PS, manufactured by Film Specialties, Inc., Whitehouse, N.J., having a permanent anti-fog coating as described in U.S. Pat. No. 4,467,073 or other similar anti-fog coating. The film has a thickness of 0.0015 inches and its coating is a two-part reactive urethane coating which prevents fogging under all temperature-humidity conditions by causing water droplets to spread, rather than form beads which appear as fog. The film has a scratch resistance which is superior to untreated plastics. Superficial scratches that do appear will heal themselves when moistened by rinsing with water or even by breathing on the film. The film is not affected by freezing, or by temperatures as high as 250 degrees Fahrenheit and its coating will not become soft when wet and will not smudge.

Flexible member 12 has an upper straight edge 14 best shown in FIGS. 2 and 6 and a pair of convex edges 16 also best shown in FIGS. 2 and 6 which are located opposite and separated from flat edge 14 on member 12. Convex edges 16 are spaced apart and joined by a concave edge 18 spaced apart from edge 14 which extends between the facing ends of convex edges 16. Each convex edge 16 and its opposite flat edge 14 portion defining a planar portion 20 which is integral with member 12. Planar portions 20 are separated by a narrowed web portion 22, also integral with member 12, defined by concave edge 18 and the portion of edge 14 opposite concave edge 18.

Convex edges 16 taper outward from web portion 22 and have their radius of curvature lessened so that edge 16 becomes almost straight as convex edges 16 extend outward towards ends 28, 30 of flexible member 12. Hence, each edge 16 and its opposite straight edge portion 14 further define plannar portions 20 having a banana shape.

Member 12 is flexible for forming an arcuate shape which is located around the head of the user (not shown) with planar portions 20 curved over the eyes of the user. Flexible member 12 has an outer surface and an inner surface facing the head of the user. A flexible sealing means is disposed along the periphery of flexible member 12 on its inner surface. The flexible sealing means includes a thin upper elongated longitudinal flexible sealing member 24 attached to the inner surface of member 12 along flat edge 14 and a thin lower elongated flexible sealing member 26 attached to the inner surface of member 12 along convex edges 16 and concave edge 18.

Upper elongated flexible sealing member 24 extends between ends 28, 30 of member 12 and has a rectangular cross section and a suitable cross sectional measurement such as ⅜ inches extending transversely to member 12, and ¼ inches along member 12. Upper elongated flexible sealing member 24 is a flexible foam rubber such as Scott industrial foam, manufactured by Merryweather or other similar type of foam. A conventional pressure sensitive adhesive (not shown) along the contacting portion of upper sealing member 24 with the inner surface of member 12 along edge 14 provides a sealing bond between upper sealing member 24 and flexible member 12.

Lower elongated flexible sealing member 26 curves along convex edges 16 and concave edge 18 and extends between ends 28, 30 of member 12. Lower elongated flexible sealing member 26 has a rectangular cross section and a suitable cross sectional measurement such as ⅜ inches extending transversely to member 12, and ¼ inches along member 12. Lower elongated flexible sealing member 26 is a flexible closed cell rubber such as Rubatex G-231-N neoprene, Rubatex Corporation, Bedford, Va., although member 26 may also be the same foam as described above. A conventional pressure sensitive adhesive (not shown) along the contacting portion of lower sealing member 26 with the inner surface of member 12 along edges 16, 18 provides a sealing bond between lower sealing member 26 and flexible member 12.

An attachment means is included with shield 10 for attaching flexible member 12 around the head of the user with planar portions 20 curved over the eyes. A preferred attachment means is shown in FIG. 1 and in detail in FIGS. 7 and 8, although other attachment means comprising latex and neoprene, for example, may be used also. The preferred attachment means as best seen in detail in FIG. 8 includes a flexible elongated adjustable band 32 which extends between ends 28, 30 of member 12 having a pair of spaced holes 34 in each of its ends. Included with the attachment means are holes 35 in ends 28, 30 of member 12 through which the ends of band 32 are passed and folded backward, as shown in FIG. 8, to align spaced holes 34 through which a fastener 36 is passed, forming a loop which passes through its respective hole 35, thus connecting band 32 to member 12. As shown in FIG. 8, fastener 36 has a circular flat button shaped base 38 from which an elongated transverse shaft 39 projects. A spherical head 40 attached to the opposite end of shaft 38 is pressed through aligned holes 34, with head 40 and base 38 retaining fastener 36 in place in holes 34 and connecting band 32 to member 12.

Elongated band 32 is of a suitable material such as rubber for flexibility and elasticity and is adjustable. Accordingly, band 32 is provided with a pair of flexible elongated members 42, 44 as shown in detail in FIG. 7 which provide for the connection between band 32 and member 12. Elongated member 42 includes a transverse opening 45 in its end through which the flexible elongated portion of member 44 frictionally extends. Elongated member 44 is provided with a pair of spaced transverse openings 46, 48 in its end through which the flexible elongated portion of member 42 frictionally extends in a woven manner by passing its elongated portion through the backside of transverse cut 46 and through the front side of transverse cut 48. Accordingly, band 32 is adjusted by moving the ends of member 42, 44 apart in the direction of ARROWS A for narrowing band 32 for smaller head sizes and is adjusted by moving the ends of members 42, 44 closer together in the direction of ARROWS B for widening band 32 for larger head sizes.

Referring to FIGS. 9-14, the second preferred embodiment of the medical shield 10' according to the present invention is shown. Shield 10' includes an elongated transparent flexible member 12' similar to member 12 and is of the same polyester film having an anti-fog coating as previously mentioned. Shield 10' includes an upper straight edge 14' similar to edge 14, convex edges 16' and a concave edge 18' similar to concave edge 18. Convex edges 16' and the portions of straight edges 14' opposite convex edges 16' define planar portions 20' which when shield 10' is flexed into an arcuate shape and located around the head of the user as shown in FIG. 18 are curved over the eyes of the user.

Planar portions 20' are similarly separated by a narrowed web portion 22' similar to web portion 22, also similarly integral with member 12'. Web portion 22 is similarly defined by concave edge 18' and the portion of edge 14' opposite concave edge 18'.

Figures 10, 11:
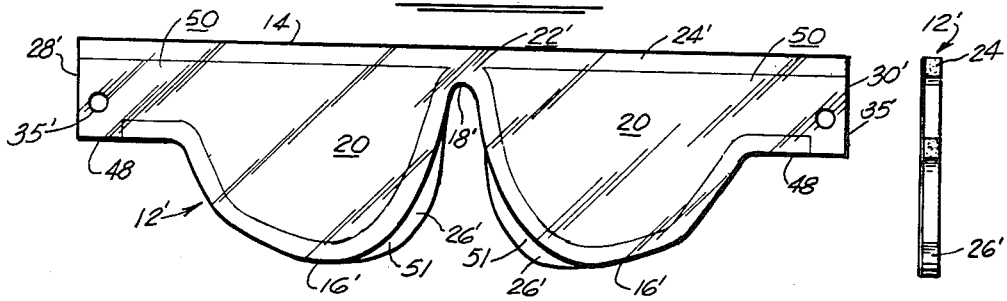
FIG. 10 is a front planar view of the transparent flexible member of the second embodiment of FIG. 9.
FIG. 11 is a side planar view of the transparent flexible member of the second embodiment of FIG. 9.
Figure 13:
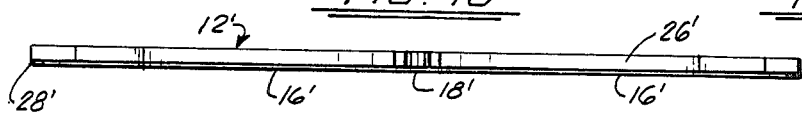
FIG. 13 is a bottom planar view of the transparent flexible member of the second embodiment of FIG. 9.
Figure 14:
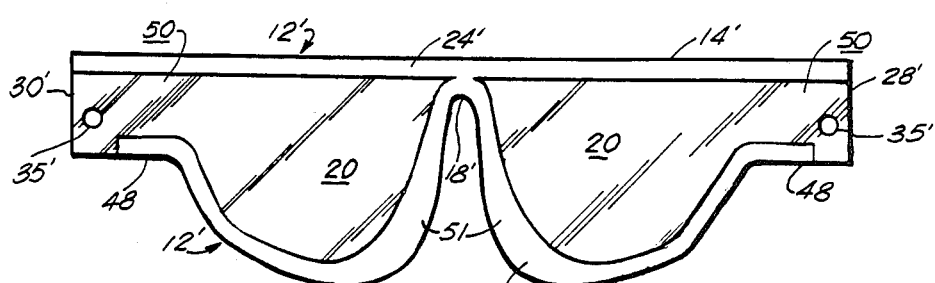
FIG. 14 is a rear planar view of the transparent flexible member of the preferred embodiment of FIG. 9.

Referring to FIGS. 10 and 14, convex edges 16' have their opposite ends curve outward and join with flat edges 48 which extend outward and parallel to flat edge 14' to each end 28', 30' of member 12' so that planar portions 20' include integral rectangular portions 50 defined by flat edges 48 and the portions of edges 14' opposite edges 48. Hence, convex edges 16' and flat edges 14', 48 further define planar portions 20' having a spectacle shape with rectangular side extensions.

Member 12' is similarly flexible for forming an arcuate shape which is located around the head of the user (FIG. 18) with planar portions 20' curved over the eyes of the user. Flexible member 12' similarly has an outer surface and an inner surface facing the head of the user. A similar flexible sealing means is disposed along the periphery of the flexible member 12 on its inner surface. The flexible sealing means includes a thin upper elongated longitudinal flexible sealing member 24' similar to sealing member 24 attached to the inner surface of member 12' along flat edge 14' and a thin lower elongated flexible sealing member 26' similar to sealing member 26 attached to the inner surface of member 12' along convex edges 16', concave edge 18' and flat edges 48.

Upper elongated flexible sealing member 24' similarly extends between ends 28', 30' of member 12' and has a rectangular cross section and a suitable cross sectional measurement such as $\frac{3}{8}$ inches extending transversely to member 12', and $\frac{1}{4}$ inches along member 12'. Upper elongated flexible sealing member 24' similarly is a flexible foam rubber such as the previously mentioned Scott industrial foam or other similar type foam. A conventional pressure sensitive adhesive (not shown) along the contacting portion of upper sealing member 24' with the inner surface of member 12' along edge 14' provides a sealing bond between upper sealing member 24' and flexible member 12'.

Lower elongated flexible sealing member 26' similarly curves along convex edges 16' and concave edge 18' and extends along flat edges 48 between ends 28', 30' of member 12'. Lower elongated flexible sealing member 26' similarly has a rectangular cross section and a suitable cross sectional measurement such as $\frac{3}{8}$ inches extending transversely to member 12', and $\frac{1}{4}$ inches along member 12'. Similarly, lower elongated flexible sealing member 26' is a flexible closed cell rubber such as previously mentioned Rubatex G-231-N neoprene although member 26' may also be the same foam as described above. A conventional pressure sensitive adhesive (not shown) along the contacting portion of lower sealing member 26' with the inner surface of member 12' along edges 16', 18', 48 provides a sealing bond between lower sealing member 26' and flexible member 12'.

Sealing member 26' includes wider bridge portions 51 which extend from the area of the ends of concave edge 18' and outward from member 12' toward each other. Bridge portions 51 widen and extend outward from member 12' for defining a deformable space therebetween which is sealable around the nose of the head of the user so that better sealing is obtained when shield 10' is used by individuals having narrower noses.

An attachment means is included with shield 10' for attaching flexible member 12' similarly around the head of the user with planar portions 20' curved over the eyes. The attachment means includes a flexible elongated adjustable band 32' similar to band 32 which extends between ends 28', 30' of member 12'.

Referring to FIGS. 15 and 16, band 32' has spaced holes 52, 54 similar to holes 34 and member 12' includes a hole 35' similar to holes 35 near each end 28', 30' of member 12'. A tab 56 extends transversely from each end of band 32' proximate hole 54 which is most distal from the end of band 32'. Each tab 56 includes a hole 58 spaced outward from distal most hole 54, allowing each tab 56 to be folded over as shown in FIG. 16 to align each hole 58 with its distal most hole 54 to form a lateral retainer 60 in the form of a loop extending transversely from band 32' through which the respective ear piece of a pair of glasses is inserted for holding the ear piece parallel and alongside band 32'. The ends of band 32 are inserted similarly through holes 35' in member 12' and folded over also as shown in FIG. 16 to align its forwardmost hole 52 with holes 54, 58 and a fastener 62 similar to fastener 36 as previously described is passed through each series of aligned holes, 52, 54, and 58 forming a loop which passes through its respective hole 35', thus connecting band 32' to member 12.

An attachment means for attaching the bridge piece of the glasses to member 12' is included. The attachment means includes an elongated flexible bridge retainer 64, best shown in FIG. 17, which is folded around web portion 22'. Flexible retainer 64 includes a female velcro portion 66 sonically welded along one end of the upper surface of retainer 64 and a corresponding male velcro fastener portion 68 mounted similarly on the undersurface of the opposite end of retainer 64. Flexible retainer 64 is folded around web portion 22' tightly as indicated by phantom lines 70 with the bridge piece of the glasses between retainer 64 and the outer surface of member 12' and velcro portions 66, 68 are pressed together and mated. Thus, the bridge piece of the glasses is retained over web portion 22' by flexible retainer 64 and the bridge piece of the glasses is lifted off of the nose of the user.

Elongated band 32' similarly is of a suitable material such as rubber for flexibility and elasticity and includes an adjustment portion as previously described. Accordingly band 32' is similarly adjusted by moving its ends apart in the direction of ARROWS C (FIG. 9) for narrowing band 32' for smaller head sizes and is adjusted by moving its ends closer together in the direction of ARROWS D (FIG. 9) for widening band 32' for larger head sizes.

In use, band 32 or 32' is sized to fit the head of the individual by moving the ends of band 32 or 32' in the directions of ARROWS A or B or C or D as previously described and the shield 12 or 12' is located on the head of the user, which may be a surgeon, surgical assistant or other medical personnel subject to receiving inadvertent foreign matter in his or her eyes from splattering of blood for example during surgical procedures, with planar portions 20 or 20' curved over the eyes and web portion 22 or 22' extending transversely across the nose. Band 32 or 32' is tightened, pressing sealing members 24, 26 or 24', 26' against body portions around the eyes, thus forming a seal between the contacting body portions around the eyes and members 24, 26 or 24' 26' preventing the bypassing of foreign matter such as splattered blood between sealing members 24, 26 or 24', 26', the contacting body portions and into the eyes.

Referring to FIG. 18, with shield 10', the second preferred embodiment of the present invention, flexible retainer 64 is folded or wrapped tightly around web portion 22' with the bridge piece 72 of the glasses 70 over the outer surface of member 12'. Velcro portions 66, 68 are pressed together and mated, thus the bridge piece 72 of the glasses 70 is retained over web portion 22' by flexible retainer 64 and the bridge piece 72 of the glasses 70 is lifted off of the nose of the user. Each ear piece 74 of the glasses 70 is inserted through the respective lateral retainer 60 and "hooked" over the ears with ear pieces 74 lying parallel and alongside band 32'. The glasses 70 are now held in position off the nose with their spectacle portions 76 lying over planar portions 20'.

After use, shield 12 or 12' is removed from the head of the user and suitably discarded along with other infected disposables.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:
1. A shield comprising:
   a. an elongated transparent flexible member having symmetrical spaced planar surfaces joined by a narrowing web portion, said member being flexible for forming an arcuate shape and including: an anti-fog coating on one of its surfaces and an upper flat edge, a pair of spaced convex edges spaced apart and located on said member opposite and spaced from said flat edge for forming said spaced planar surfaces, said planar portions extended between said flat edge and said convex edge, said convex edges being joined by a concave edge located on said member opposite said flat edge and between said convex edges for defining said narrowing web portion, said web portion extended integrally between said planar portions, said convex edges have their opposite ends curving outward and joining with a flat edge extending outward and paralleling said straight edge to opposite ends of said flexible member;
   b. attachment means form attaching said flexible member in an arcuate shape around the head of a human with said spaced surfaces located above and covering the eyes and said narrowing web portion extending transversely across the nose, said attachment means being an elongated band extending between the ends of said flexible member, said elongated band including retaining means extending from said band proximate each end of said flexible member forming a pair of retainer means through which the ear pieces of a pair of glasses are inserted for holding the ear pieces parallel and alongside said band; and,
   c. flexible sealing means disposed along the periphery of said flexible member for forming a seal between said flexible member and the body portion around the eyes, said sealing means extending outward from said narrowing web portion toward the edges of said arcuate shape and including: an upper elongated deformable flexible sealing member extending along said flat edge between the distal ends of said flexible member and a second elongated deformable flexible sealing member extending continuously along said convex edges and said concave edge between the distal ends of said flexible member.

2. The shield of claim 1, wherein said attachment means includes first and second elongated parallel portions, each of said elongated parallel portions being attached at one of their ends to the opposite ends of said flexible member, said first elongated portion including a transverse cut in its free end through which said second elongated parallel portion extends, said second elongated parallel portion including spaced transverse cuts in its free end through which said first elongated parallel portion is woven, said elongated parallel portions being movable in said transverse cuts for adjusting the length of said attachment means.

3. The shield of claim 1, wherein each of said convex edges tapers outwards from said web portion, each of said convex edges becoming almost straight as said convex edges extend outward toward the ends of said flexible member for defining spaced planar portions having a banana shape.

4. The shield of claim 1, wherein each retainer means is a tab extending transversely from each end of said band proximate said flexible member, said tab being folded over and attached at its free end to said band by a fastener means for providing a loop which extends transversely from said band through which said ear piece is inserted.

5. The shield of claim 4, said shield further comprising an attachment means disposed over said web portion for attaching the bridge piece of said glasses over said web portion of said flexible member.

6. The shield of claim 5, wherein said attachment means is an elongated flexible member folded around said web portion, said elongated flexible member having fastening means attached to the ends of said elongated flexible member engageable when said flexible member is folded around said web portion tightly with said bridge piece between said flexible member and said web portion for retaining said bridge piece over said web portion and off the nose of the head.

7. A shield comprising:
   a. a thin elongated transparent flexible member having an upper flat edge, a pair of spaced convex edges apart and located on said member opposite and spaced from said flat edge for forming a pair of spaced planar portions, said planar portions extending between said flat edge and said convex edges, said convex edges being joined by a concave edge located on said member opposite said flat edge and between said convex edges for defining a narrowed webbed portion, said webbed portion extending integrally between said planar portions, said convex edges have their opposite ends curving outward and joining with a flat edge extending outward and paralleling said straight edge to opposite ends of said flexible member;

b. a first elongated deformable flexible sealing member extending along said flat edge between the distal ends of said flexible member;

c. a second elongated deformable flexible sealing member extending continuously along said convex edges and said concave edge between the distal ends of said flexible member; and, d. an elongated band extending between the distal ends of said flexible member for attaching said flexible member in an arcuate shape around the head of a human with said spaced surfaces located above and covering the eyes and said webbed portion extending transversely across the nose, said sealing members contacting and sealing against the body portions surrounding the eyes along the length of said seal members for isolating the eyes from airborne matter, said elongated band including retaining means extending from said band proximate each end of said flexible member forming a pair of retainer means through which the ear pieces of a pair of glasses are inserted for holding the ear pieces parallel and alongside said band.

8. The shield of claim 7, wherein said attachment means includes first and second elongated parallel portions, each of said elongated parallel portions being attached at one of their ends to the opposite ends of said flexible member, said first elongated portion including a transverse cut in its free end through which said second elongated parallel portion extends, said second elongated parallel portion including spaced transverse cuts in its free end through which said first elongated parallel portion is woven, said elongated parallel portions being movable in said transverse cuts for adjusting the length of said attachment means.

9. The shield of claim 7, wherein each of said convex edges tapers outwards from said web portion, each of said convex edges becoming almost straight as said convex edges extend outward toward the ends of said flexible member for defining spaced planar portions having a banana shape.

10. The shield of claim 7, wherein each retainer means is a tab extending transversely from each end of said band proximate said flexible member, said tab being folded over and attached at its free end to said band by a fastener means for providing a loop which extends transversely from said band through which said ear piece is inserted.

11. The shield of claim 10, said shield further comprising an attachment means disposed over said web portion for attaching the bridge piece of said glasses over said web portion of said flexible member.

12. The shield of claim 11, wherein said attachment means is an elongated flexible member folded around said web portion, said elongated flexible member having fastening means attached to the ends of said elongated flexible member engageable when said flexible member is folded around said web portion tightly with said bridge piece between said flexible member and said web portion for retaining said bridge piece over said web portion and off the nose of the head.

13. A shield comprising:

a. a thin elongated transparent flexible member having an upper flat edge, a pair of spaced convex edges spaced apart and located on said member opposite said flat edge for forming a pair of spaced planar portions, said planar portions extending between said flat edge and said convex edges, said convex edges being joined by a concave edge located on said member opposite said flat edge and between defining a narrowed webbed portion, said webbed portion extending integrally between said planar portions;

b. an elongated deformable flexible sealing member extending along said flat edge between the distal ends of said flexible member;

c. a second elongated deformable flexible sealing member extending continuously along said convex edges and said concave edge between the distal ends of said flexible member;

d. an elongated band connected between the distal ends of said flexible member for attaching said flexible member in an arcuate shape around the head of a human with said spaced surfaces located above and covering the eyes and said webbed portion extending transversely across the nose, said sealing members contacting and sealing against the body portions surrounding the eyes along the length of said seal members for isolating the eyes from airborne matter; and, e. a flexible tab extending transversely from said band proximate each end of said flexible member positionable around the elongated ear piece of a pair of glasses for retaining said ear piece longitudinally along said band.

14. The shield of claim 13, wherein said flexible member includes an anti-fog coating on one of its surfaces.

15. The shield of claim 14, wherein said attachment means includes first and second elongated parallel portions, each of said elongated parallel portions being attached at one of their ends to the opposite ends of said flexible member, said first elongated portion including a transverse cut in its free end through which said second elongated parallel portion extends, said second elongated parallel portion including spaced transverse cuts in its free end through which said first elongated parallel portion is woven, said elongated parallel portions being movable in said transverse cuts for adjusting the length of said attachment means.

16. The shield of claim 14, wherein said convex edge their opposite ends curving outward and joining with a flat edge extending outward and paralleling said straight edge to opposite ends of said flexible member.

17. The shield of claim 16, said shield further comprising an attachment means disposed over said web portion for attaching the bridge piece of said glasses over said web portion of said flexible member.

18. The shield of claim 17, wherein said attachment means is an elongated flexible member folded around said web portion, said elongated flexible member having fastening means attached to the ends of said elongated flexible member engageable when said flexible member is folded around said web portion tightly with said bridge piece between said flexible member and said web portion for retaining said bridge piece over said web portion and off the nose of the head.

19. The shield of claim 13, wherein said second elongated deformable flexible sealing member includes widening spaced bridge portions, said bridge portions extending from the area of said concave edge and outward toward each other for defining a deformable space therebetween, sealable around the nose of the head.

* * * * *